US010421714B2

(12) United States Patent
Bristow

(10) Patent No.: US 10,421,714 B2
(45) Date of Patent: Sep. 24, 2019

(54) PROCESS FOR PREPARING MESOTRIONE

(71) Applicant: Rotam Agrochem International Company Limited, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 15/174,756

(22) Filed: Jun. 6, 2016

(65) Prior Publication Data

US 2016/0355472 A1 Dec. 8, 2016

(30) Foreign Application Priority Data

Jun. 8, 2015 (GB) .................................. 1509854.4

(51) Int. Cl.
C07C 315/04 (2006.01)
C07C 315/06 (2006.01)

(52) U.S. Cl.
CPC .......... C07C 315/04 (2013.01); C07C 315/06 (2013.01)

(58) Field of Classification Search
CPC ..................................................... C07C 43/23
See application file for complete search history.

(56) References Cited

U.S. PATENT DOCUMENTS

| 4,695,673 | A | 9/1987 | Heather et al. |
| 5,728,889 | A | 3/1998 | Rawlinson et al. |
| 5,912,207 | A | 6/1999 | Scher et al. |
| 7,820,863 | B2 * | 10/2010 | Wichert ................ C07C 315/04 568/30 |

FOREIGN PATENT DOCUMENTS

| CN | 1860102 A | 11/2006 |
| CN | 103772243 A | 5/2014 |
| EP | 1740534 B1 | 11/1997 |
| EP | 1377544 B1 | 9/2000 |
| EP | 1034159 B1 | 1/2004 |
| EP | 0805792 B1 | 1/2007 |
| WO | 2005035487 A1 | 4/2005 |
| WO | 2006021743 A1 | 3/2006 |
| WO | 2007083242 A1 | 7/2007 |
| WO | 2011005127 A1 | 1/2011 |

OTHER PUBLICATIONS

Written Opinion dated Sep. 7, 2016.
International Search Report for PCT/CN2016/085035 dated Sep. 13, 2016.

* cited by examiner

Primary Examiner — Rosalynd A Keys
(74) Attorney, Agent, or Firm — Dickinson Wright PLLC

(57) ABSTRACT

A process for the preparation of mesotrione enolate is provided. The process comprises providing a solution of mesotrione in an organic solvent and contacting the solution with a moderate base in the presence of water at a pH of from 6 to 8, to form an aqueous mesotrione enolate solution. A process for preparing mesotrione from the products of an enol ester rearrangement of 3-oxocyclohex-1-enyl-4-(methylsulfonyl)-2-nitrobenzoate is also provided. The process comprises contacting the products of the rearrangement reaction with an organic solvent to dissolve mesotrione; and contacting the resulting solution with an aqueous solution of an acid.

27 Claims, No Drawings

PROCESS FOR PREPARING MESOTRIONE

This US patent application claims priority to GB patent application no.: GB1509854.4, filed Jun. 8, 2015, the entire content of which is incorporated herein by reference.

BACKGROUND

1. Field

The present invention relates to various aspects of a novel process scheme for the preparation of acylated 1,3-dicarbonyl compounds, and in particular, to a process scheme for producing herbicidal acylated 1,3-dicarbonyl compounds, more particularly to methods for producing the selective herbicide mesotrione.

1. Related Art

2-[4-(methanesulfonyl)-2-nitrobenzoyl]cyclohexane-1,3-dione is a triketone having the common name 'mesotrione'. Mesotrione is a herbicide having activity as a HPPD inhibitor. Formulations of mesotrione are known in the art and are commercially available.

Mesotrione has the following chemical structure:

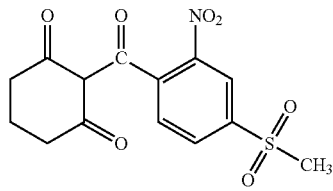 [SMILES: CS(=O)(=O)c1ccc(C(=O)C2C(=O)CCCC2=O)c([N+](=O)[O-])c1]

Processes for the preparation of mesotrione are known in the art.

For example, U.S. Pat. No. 4,695,673 relates to various acylated 1,3-dicarbonyl compounds prepared by rearranging certain enol esters. These compounds include cyclohexanediones, where the acylating moiety is a benzoyl group which may be substituted with a wide range of different substituents. The enol rearrangement is carried out in the presence of a catalytic amount of a cyanide moiety, such as hydrogen cyanide, an alkaline earth metal cyanide, or a cyanide derivative, such as a cyanohydrin, and a molar excess of a moderate base, such as a trialkylamine, an alkali metal carbonate, or a corresponding phosphate.

U.S. Pat. No. 5,728,889 discloses a process for producing 2-(substituted benzoyl)-1,3-cyclohexanediones that does not require cyanide anion to effect the enol ester rearrangement. The process employs a reaction medium containing a base, such as a trialkylamine, an alkali metal carbonate, or a phosphate, and a polar aprotic solvent, such as dimethylformamide, that is substantially free of hydrogen cyanide or a cyanide anion.

U.S. Pat. No. 5,912,207 relates to transition metal chelates of herbicidal dione compounds, such as mesotrione, which are prepared by adding an aqueous solution of a transition metal ion to the dione compound in water or an organic solvent.

EP 0 805 792 discloses a process for the preparation of 2-(substituted benzoyl)-1,3 cyclohexanediones. The process employs a rearrangement reaction to form the desired 2-(substituted benzoyl)-1,3 cyclohexanedione, in the presence of a non-polar solvent, a cyanide source, an alkali or alkaline earth metal carbonate, a phase transfer catalyst and water.

EP 1 034 159 discloses a process for the preparation of acylated cyclic 1,3-dicarbonyl compounds, including mesotrione. This process also employs a rearrangement reaction and is conducted in a polar aprotic, dipolar aprotic or aromatic hydrocarbon solvent and in the presence of a moderate base and a defined azole compound, for example 1,2,4-triazoles and related analogues. In the case of mesotrione, 1-(2-nitro-4-methanesulphonylbenzoyl)-1,2,4-triazole is reacted with cyclohexan-1,3-dione in the presence of potassium carbonate suspended in acetonitrile. Acetonitrile is removed from the resulting mixture under reduced pressure, the residue dissolved in water and acidified with hydrogen chloride solution. The solution is then extracted with dichloromethane, dried, filtered and the solvent removed under reduced pressure.

Attention has also been paid in the prior art to processes preparing mesotrione and similar compounds in a purer form.

For example, EP 1 377 544 discloses a process for the purification of 2-nitro-4-methylsulfonylbenzoic acid (NMSBA), an intermediate of use in the preparation of mesotrione. The process comprises, in order, dissolving NMSBA in water at a pH of 2 to 10, followed by filtration, optionally contacting the solution of NMSBA with activated carbon at a pH of from 2 to 10; treating the aqueous solution of NMSBA with sufficient base to hydrolyse undesired nitro and dinitro substituted impurities; followed by maintaining the resulting aqueous solution of NMSBA at a temperature of up to 95° C. and adjusting the pH of the solution to a pH sufficient to effect crystallization of NMSBA upon cooling.

A process for the purification of mesotrione is disclosed in EP 1 740 534. The process is aimed at reducing the cyanide levels in a mesotrione sample, arising from the use of acetone cyanohydrin as a catalyst in the rearrangement reaction forming mesotrione. The process disclosed comprises forming an aqueous solution of mesotrione, adjusting the pH of the solution to a value of 9.5 or higher, and crystallising mesotrione out of solution.

Further, WO 2005/035487 discloses a process for purifying mesotrione. The process comprises the steps of forming an aqueous mesotrione enolate solution, performing one ore more purification processes on the solution, and thereafter crystallising the purified mesotrione from the aqueous solution.

The enolate solution may be formed by the addition of an appropriate base. A pH of from 6 to 13 is maintained when forming the enolate solution. However, the teaching of WO 2005/035487 is that strong bases must be used in order to attain alkaline conditions having high pH values in the range of from 9.5 to 13. Values of pH in this range are used in all the specific examples of WO 2005/035487. Suitable purification processes are filtration or adsorption with a suitable sorbent, followed by extraction and decantation using an organic solvent.

WO 2007/083242 discloses a process for the cyrstallization of mesotrione. The process comprises introducing an aqueous solution of mesotrione into a crystallizer. Seed crystals are added to the crystallizer to seed the crystal growth. The seed crystals are predominantly of the Form I polymorph. The aforementioned process is also described as being of use for converting the Form II polymorph of mesotrione to the more stable Form I polymorph, by way of crystallization.

WO 2006/021743 discloses a process for the preparation of polymorphs of mesotrione. The process employs crystallization of mesotrione. Control of the pH of the solution during crystallization is said in WO 2006/021743 to allow the Forms I or II of mesotrione to be selectively obtained.

SUMMARY

There is a need for an improved process for the preparation of mesotrione. In particular, it would be advantageous if the process could prepare mesotrione in high yields and purity, with only low amounts of impurities present. It would also be advantageous if the process scheme could be simple to operate, in particular on a large or commercial scale, and employ reactants and other processing components that are safe and easy to handle without operational hazards, reducing or avoiding the need for toxic reagents and processing components and the need for harsh operating conditions.

An improved process scheme for the preparation of mesotrione has now been found. The process scheme is a multistage process and comprises a number of different processing steps. Improvements have been found in a number of different aspects of the process scheme. As a result, an improved process scheme for the preparation of mesotrione has been found that is particularly advantageous when applied on a commercial scale.

DETAILED DESCRIPTION OF EXAMPLE EMBODIMENTS

In a first aspect, it has now been found that, in contrast to the teaching of the prior art, as discussed above, mesotrione enolate is advantageously formed in aqueous solution from mesotrione by the application of a weak base and at a pH of from 6 to 8.

Accordingly, in a first aspect, the present invention provides a process for the preparation of mesotrione enolate, the process comprising providing a solution of mesotrione in an organic solvent and contacting the solution with a moderate base in the presence of water at a pH of from 6 to 8, to form an aqueous mesotrione enolate solution.

The preparation of mesotrione enolate according to the first aspect of the present invention is particularly useful in a process scheme for the preparation of mesotrione having a high purity. More specifically, the process of this aspect of the present invention is advantageous in removing cyanide impurities remaining in the mesotrione as a result of the mesotrione synthesis process employed. Such cyanide impurities are generated during the preparation of mesotrione by an enol ester rearrangement reaction of the corresponding benzoate, 3-oxocyclohex-1-enyl-4-(methylsulfonyl)-2-nitrobenzoate.

In contrast to the processes of the prior art, which employ alkali conditions having a high pH, in particular in excess of pH 9.5, it has surprisingly been found that the use of a moderate base and conditions having a pH of from 6 to 8, is very suitable for forming a mesotrione enolate aqueous solution, from which mesotrione can be precipitated with a high purity. This is an advantage when operating the process, in particular on a commercial scale, as the moderately basic materials required are much easier to handle and the reaction conditions are safer and less corrosive of the processing equipment, in turn allowing simpler apparatus to be employed in conducting the process and handling the reaction components, leading to a reduction in the manufacturing costs.

In the process of the first aspect of the present invention, mesotrione is provided in solution in a suitable organic solvent. Suitable organic solvents are known in the art and are commercially available. Ethers are one preferred class of organic solvents, with simple ethers and petroleum ether being preferred. Preferred ethers include diethyl ethers, dimethyl ethers, dipropyl and diisopropyl ethers, butyl ethers and pentyl ethers. Petroleum ether is a particularly preferred organic solvent.

Another preferred class of solvents are haloalkanes, in particular haloalkanes having from 1 to 10 carbon atoms, more preferably from 1 to 8 carbon atoms, still more preferably from 1 to 6 carbon atoms. The haloalkanes may be straight chain, branched chain or cyclic. A preferred halogen substituent for the haloalkanes is chlorine. Preferred haloalkanes include mono-, di- and tri-substituted alkanes. Examples of preferred haloalkanes are dichloromethane, dichloroethanes, dichloropropanes, dichlorobutanes and dichloropentanes.

A further preferred class of solvents are the alkanes and cycloalkanes, in particular having from 3 to 10 carbon atoms, more preferably from 4 to 8 carbon atoms. The alkanes may be straight chain or branched. In particular, preference is given to $C_6$ alkanes, especially hexane and cyclohexane.

In addition, organic nitriles are preferred solvents, in particular nitriles having from 2 to 6, more preferably from 2 to 4 carbon atoms. Acetonitrile is a particularly preferred nitrile solvent.

Petroleum ether and cyclohexane are particularly preferred solvents, with cyclohexane being especially preferred.

The mesotrione enolate is formed in the presence of a moderate base. Suitable moderate bases for use in the process are known in the art and are commercially available. In this respect, a moderate base is a substance that acts as a base, but whose strength of activity as a base lies between that of strong bases, such as hydroxides, and that of weak bases, such as N,N-dimethylaniline. Moderate bases that may be employed include organic bases, such as trialkylamines, or inorganic bases, such as alkali metal and alkali earth metal carbonates and phosphates. One preferred group of moderate bases are the alkali metal carbonates and alkali earth metal carbonates, with potassium carbonate being especially preferred.

In the process of this aspect of the present invention, the meostrione enolate is formed under mild pH conditions, that is at a pH of from 6 to 8. The pH in this range is preferably at least 6.1, more preferably at least 6.2, still more preferably at least 6.3, more preferably still at least 6.4, with a pH of at least 6.5 being preferred, more especially a pH of at least 6.6. The pH in the aforementioned range is preferably no greater than 7.8, more preferably no greater than 7.6, still more preferably no greater than 7.5, more preferably still no greater than 7.4, more especially no greater than 7.3. A preferred pH range is from 6 to 7.5. A pH of from 6 to 7.2 is more preferred, more preferably a pH of from 6.2 to 7, with a pH of from 6.5 to 7 being especially preferred, with a pH of from 6.7 to 6.9 being particularly preferred. A pH of about 6.8 has been found to be particularly suitable.

The mesotrione and moderate base may be present in any suitable ratio. However, it has been found that a molar ratio of mesotrione to the moderate base of 1:1 or less is very suitable. It is preferred that the mesotrione is present in a slight molar excess to the moderate base, preferably at a molar ratio of from 0.75 to 0.95. A molar ratio of mesotrione to the moderate base of about 1:0.8 is particularly preferred.

In the process of the first aspect of the present invention, mesotrione enolate is formed at the interface between the organic phase and the aqueous phase and enters the aqueous phase. The aqueous phase may then be separated and the mesotrione recovered in high yields with a high purity. Complicated purification techniques, such as distillation and/or extraction, are not required and can be avoided.

Surprisingly, it has been found that by operating the process in the pH range of from 6 to 8, mesotrione is converted in high amounts to the enolate salt and enters the aqueous phase, while the impurities present in the reaction medium remain in the organic phase. It is then a simple matter to separate the organic phase containing the impurities from the aqueous phase. The organic phase may be easily and safely discarded or further processed, leaving essentially pure mesotrione enolate salt in aqueous solution. It has been found that operation at a higher pH results in a significant amount of the impurities also being converted into a salt and entering the aqueous phase. This in turn requires further purification of the aqueous phase, in particular to remove the impurities.

As noted above, the process of the first aspect of the present invention is particularly useful in purifying a raw mesotrione material, in particular to remove impurities, such as cyanide compounds. Accordingly, this allows the mesotrione to be prepared by a rearrangement reaction, in particular by the enol ester rearrangement of 3-oxocyclohex-1-enyl-4-(methylsulfonyl)-2-nitrobenzoate.

It has been found that the treatment of the raw mesotrione formed by the aforementioned rearrangement reaction can affect the stability of the mesotrione product. More specifically, it has been found that the stability of the mesotrione product can be significantly increased if, once the rearrangement reaction has completed, the mesotrione is rapidly dissolved in an organic solvent and washed with an aqueous solution of an acid.

Accordingly, in a second aspect of the present invention, there is provided a process for preparing mesotrione from the products of an enol ester rearrangement of 3-oxocyclohex-1-enyl-4-(methylsulfonyl)-2-nitrobenzoate, the process comprising:

contacting the products of the said rearrangement reaction with an organic solvent to dissolve mesotrione; and contacting the resulting solution with an aqueous solution of an acid.

The products of the process of the second aspect of the present invention may be employed directly in the process of the first aspect of the present invention.

It has been found that by washing the mesotrione-containing products of the enol ester rearrangement reaction, the mesotrione product is more stable, compared with contacting the rearrangement products directly with a base. Dissolving the mesotrione in an organic solvent also assists in stabilizing the mesotrione product.

In the process of the second aspect of the present invention, mesotrione produced by the rearrangement reaction is dissolved in a suitable organic solvent. Suitable organic solvents are known in the art and are commercially available.

Ethers are one preferred class of organic solvents, with simple ethers and petroleum ether being preferred. Preferred ethers include diethyl ethers, dimethyl ethers, dipropyl and diisopropyl ethers, butyl ethers and pentyl ethers. Petroleum ether is a particularly preferred solvent from this class.

Another preferred class of solvents are haloalkanes, in particular haloalkanes having from 1 to 10 carbon atoms, more preferably from 1 to 8 carbon atoms, still more preferably from 1 to 6 carbon atoms. The haloalkanes may be straight chain, branched chain or cyclic. A preferred halogen substituent for the haloalkanes is chlorine. Preferred haloalkanes include mono-, di- and tri-substituted alkanes. Examples of preferred haloalkanes are dichloromethane, dichloroethanes, dichloropropanes, dichlorobutanes and dichloropentanes.

A further preferred class of solvents are the alkanes and cycloalkanes, in particular having from 3 to 10 carbon atoms, more preferably from 4 to 8 carbon atoms. The alkanes may be straight chain or branched. In particular, preference is given to $C_6$ alkanes, especially hexane and cyclohexane.

In addition, organic nitriles are preferred solvents, in particular nitriles having from 2 to 6, more preferably from 2 to 4 carbon atoms. Acetonitrile is a particularly preferred nitrile solvent.

A further class of suitable solvents is the organic amides, preferably $C_1$ to $C_6$ alkylamides, more preferably $C_1$ to $C_4$ alkylamides. Alkyl and di-alkyl acid amides are preferred, with dimethyl acid amides being particularly preferred solvents. One preferred solvent is N,N-dimethylformamide (DMF).

A still further class of suitable solvents is the alkyl and di-alkyl sulfonamides, in particular $C_1$ to $C_6$ alkyl or di-alkyl sulfonamides. One preferred solvent from this class is dimethylsulfonamido (DMSO).

Petroleum ether and cyclohexane are particularly preferred solvents, with cyclohexane being especially preferred.

It is most preferred that the solvent is added to the entire reaction mixture produced by the enol ester rearrangement reaction.

The resulting solution of mesotrione is washed with an aqueous solution of an acid. Suitable acids for use in this step are known in the art and are commercially available. Inorganic acids are very suitable. Suitable acids include mineral acids, especially sulphuric acid, nitric acid and hydrochloric acid. A preferred acid is hydrochloric acid.

The aqueous acid solution may have any suitable strength and is preferably moderately acidic. The aqueous acid solution may be from 1N to 3N, more preferably from 1.5N to 2.5 N. A 2N solution of the acid is particularly suitable.

As noted above, the process of the second aspect of the present invention is applied to the mesotrione product of an enol ester rearrangement of 3-oxocyclohex-1-enyl-4-(methylsulfonyl)-2-nitrobenzoate. An improved rearrangement process has now been found for the preparation of mesotrione.

Accordingly, in a third aspect, the present invention provides a process for the preparation of mesotrione, the process comprising:

conducting an enol ester rearrangement of 3-oxocyclohex-1-enyl-4-(methylsulfonyl)-2-nitrobenzoate by forming a reaction mixture comprising 3-oxocyclohex-1-enyl-4-(methylsulfonyl)-2-nitrobenzoate, an organic solvent, a moderate base sufficient to obtain mesotrione, and a cyanide ion source, wherein the enol ester rearrangement is carried out in the absence of a phase transfer catalyst, a transition metal salt and an azole.

In the process of the third aspect of the present invention, the reaction mixture comprises an organic solvent. Any suitable organic solvent may be used and suitable solvents are known in the art. Polar organic solvents are preferred, more preferably polar aprotic solvents. Organic nitriles are preferred solvents, in particular nitriles having from 2 to 6, more preferably from 2 to 4 carbon atoms. One preferred solvent is acetonitrile.

The reaction mixture further comprises a moderate base. Suitable moderate bases for use in the process are known in the art and are commercially available. In this respect, a moderate base is a substance that acts as a base, but whose strength of activity as a base lies between that of strong bases, such as hydroxides, and that of weak bases, such as N,N-dimethylaniline. Moderate bases that may be employed include organic bases, such as trialkylamines, or inorganic bases, such as alkali metal carbonates and phosphates. One preferred group of moderate bases are the alkylamines, preferably trialkylamines, with triethylamine being particularly preferred. Another preferred group of moderate bases are the alkali metal carbonates, with potassium carbonate being especially preferred. The alkali metal carbonates are employed in the form of an aqueous solution, for example a 1 to 10% by weight aqueous solution, more preferably about 5% by weight aqueous solution.

The 3-oxocyclohex-1-enyl-4-(methylsulfonyl)-2-nitrobenzoate and moderate base may be present in any suitable ratio, for example a molar ratio of 3-oxocyclohex-1-enyl-4-(methylsulfonyl)-2-nitrobenzoate to the moderate base from 1:4 to 4:1, more preferably from 1:2 to 2:1. A molar ratio of 3-oxocyclohex-1-enyl-4-(methylsulfonyl)-2-nitrobenzoate to the moderate base of about 1:1 is particularly preferred.

The rearrangement reaction takes place in the presence of a cyanide ion source as a catalyst. A 'cyanide ion source' refers to a substance or substances which under rearrangement conditions consist of or generate hydrogen cyanide and/or cyanide anions. Cyanohydrins are a preferred class of cyanide sources, in particular acetone cyanohydrin.

Without wishing to be bound by any theory, it is believed that a possible mechanism for this process is shown as follows:

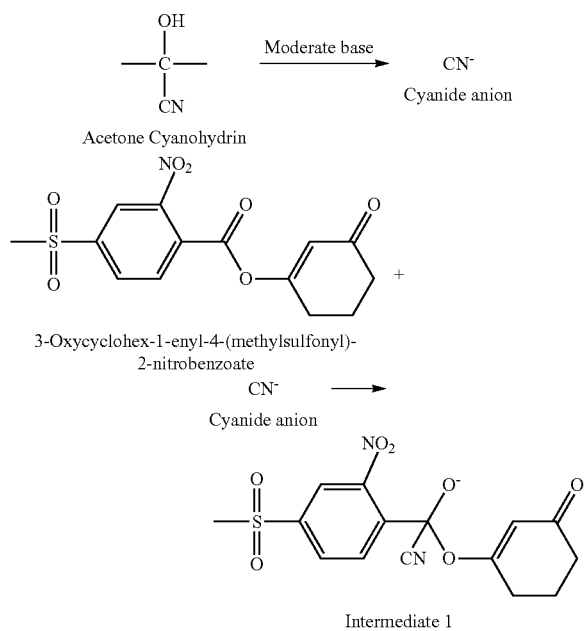

Firstly, the cyanide ion source, such as acetone cyanohydrin, generates cyanide anions with the presence of the moderate base, such as triethyl amine, which then attack the carbonyl group of the enol ester to produce the intermediate 1. The intermediate 1 then undergoes cleavage of the C—O bond to form intermediate 2 and the carbonide anion of 1,3-cyclohexanedione as shown below:

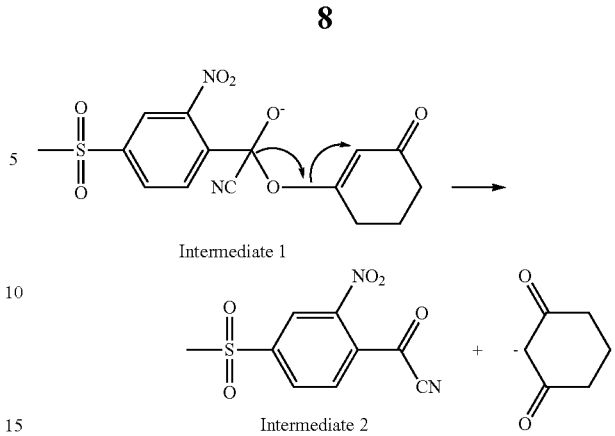

The carbonide anion of 1,3-cyclohexanedione then attacks the carbonyl group of the intermediate 2 (benzoyl cyanide) and produces the final product mesotrione, as follows:

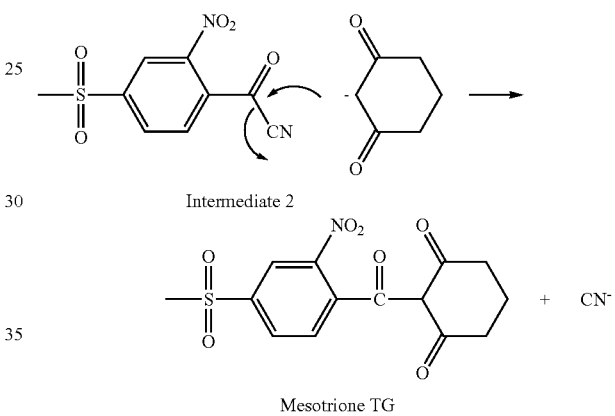

The 3-oxocyclohex-1-enyl-4-(methylsulfonyl)-2-nitrobenzoate used as the starting material in the process of the third aspect of the present invention may be prepared by the reaction of a 4-(methanesulfonyl)-2-nitrobenzoyl halide, preferably 4-(methanesulfonyl)-2-nitrobenzoyl chloride (NMSBC), with cyclohexane-1,3-dione in an organic solvent, in the presence of an organic base.

Suitable organic solvents for performing the reaction are known in the art. A preferred group of organic solvents are the haloalkanes, preferably halo-$C_1$ to $C_8$ alkanes, more preferably halo-$C_1$ to $C_6$ alkanes. Chlorinated alkanes are particularly preferred. Preferably, the organic solvent is a halomethane, such as chloroform, or di- or tri-chloro alkanes, where the alkane is methane, ethane, propane, butane or pentane. Dichloromethane is especially preferred.

The organic base is preferably an alkylamine, more preferably a trialkylamine. Trimethylamine is a particularly preferred base.

Once the reaction has completed, the resulting reaction mixture containing 3-oxocyclohex-1-enyl-4-(methylsulfonyl)-2-nitrobenzoate is preferably subjected to one or more washing steps. In one preferred regime, the resulting mixture is washed sequentially with an aqueous solution of an acid, preferably hydrochloric acid, water, an aqueous solution of a moderate base, preferably potassium carbonate, and saturated sodium chloride solution.

The organic phase is then recovered and dried to remove any water. Thereafter, the organic solvent is removed, for example under a vacuum.

The 4-(methanesulfonyl)-2-nitrobenzoyl halide, for example 4-(methanesulfonyl)-2-nitrobenzoyl chloride (NMSBC), may be prepared by the reaction of 4-(methylsulfonyl)-2-nitrobenzoic acid (NMSBA) with a thionyl halide, such as thionyl chloride, in the presence of an organic solvent, such as a mixture of dichloroethane and N,N-dimethyl formamide.

In one preferred embodiment, 4-(methanesulfonyl)-2-nitrobenzoyl chloride (NMSBC) is prepared by reaction of 4-(methylsulfonyl)-2-nitrobenzoic acid (NMSBA) in dichloroethane by refluxing with N,N-dimethyl formamide (DMF) and thionyl chloride.

During the reaction, sulphur dioxide and hydrogen halide, in particular hydrogen chloride, are preferably removed from the reaction mixture.

Once the reaction has completed, the solvent and unreacted thionyl chloride are preferably removed, for example under reduced pressure at a temperature below 60° C. Preferably, thionyl chloride is present in the final product in an amount of less than 0.1% by weight.

4-(methylsulfonyl)-2-nitrobenzoic acid (NMSBA) may be prepared by a variety of methods known in the art, for example as described in 'The Chemistry of Carboxylic Acids and Esters', S. Patai, editor, J. Wiley and Sons, New York, N.Y. (1969) and 'Survey of Organic Synthesis', C. A. Buehler and D. F. Pearson, J. Wiley and Sons (1970).

Suitable methods for preparing 4-(methylsulfonyl)-2-nitrobenzoic acid (NMSBA) include the following:

(a) oxidize the corresponding substituted ethyl group by contact with an aqueous solution of potassium permanganate, as follows:

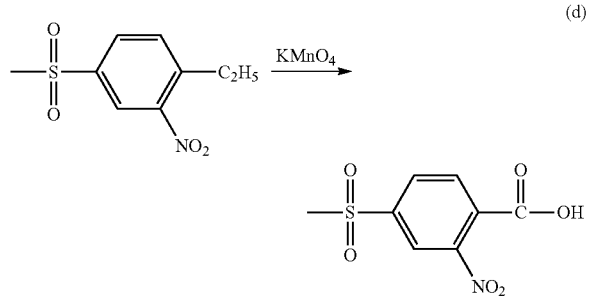

(b) contacting 1-cyano-2-nitro-4-methylsulphonyl benzene with aqueous sulfuric acid, as follows:

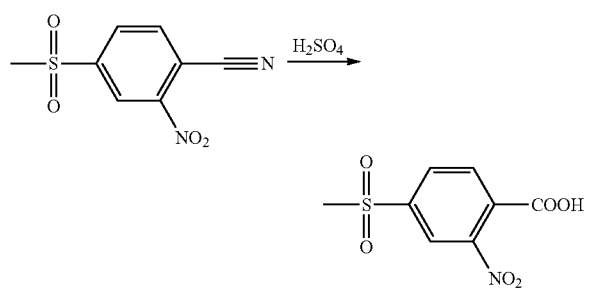

(c) oxidize the corresponding substituted acetophenone by contact with an aqueous hypochlorite solution, as follows:

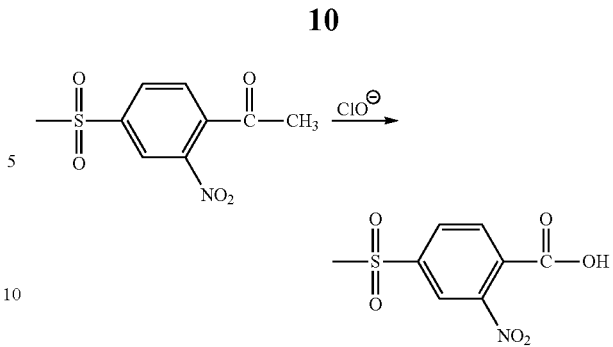

(d) oxidize the corresponding substituted toluene group by contact with an aqueous solution of potassium permanganate, as follows:

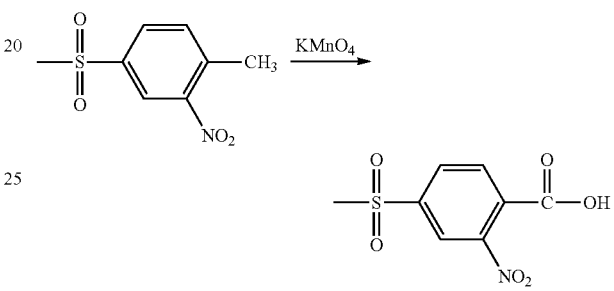

Other oxidizing agents that may be used to form 4-(methylsulfonyl)-2-nitrobenzoic acid (NMSBA) include chromic acid, potassium dichromate and dilute hydrochloric acid.

Surprisingly, it has been found that 4-(methylsulfonyl)-2-nitrobenzoic acid (NMSBA) prepared using methods (a) to (c) are all particularly suitable, in terms of both yield and purity, for use in the general process scheme according to embodiments of the present invention. In particular, methods (a) to (c) result in a reduction in the impurities present in the product mixture and have the advantage of avoiding the need for conducting the reaction under high pressure, as is the case with methods in the prior art.

The 4-(methylsulfonyl)-2-nitrobenzoic acid (NMSBA) product of methods (a) to (c) may be used directly in the further processing steps to prepare mesotrione. More preferably, it is preferred to recover and purify the 4-(methylsulfonyl)-2-nitrobenzoic acid (NMSBA) before being used in the further processing to form mesotrione.

There are a range of techniques known in the art for purifying 4-(methylsulfonyl)-2-nitrobenzoic acid (NMSBA). For example, U.S. Pat. No. 5,591,890 teaches dissolving 4-(methylsulfonyl)-2-nitrobenzoic acid (NMSBA) in an aqueous medium with a base, such as sodium carbonate at a pH in the range of from 2 to 10. The product is recovered by filtration.

It has been found that re-crystallization of 4-(methylsulfonyl)-2-nitrobenzoic acid (NMSBA) from solution is also an effective method to purify the product. The 4-(methylsulfonyl)-2-nitrobenzoic acid (NMSBA) is preferably dissolved in an organic solvent, from which the purified product may be recovered by recrystallization. Suitable solvents include the halogenated alkanes, ethers and alkanes mentioned hereinbefore. Preferred solvents include dichloromethane, trichloromethane and dichloroethanes, methyl tert-butyl ether, cyclohexane and petroleum ether.

In addition, it has been found that sorbents, such as silicates, for example magnesium silicate (available commercially as Florisil®) may also be used to purify the 4-(methylsulfonyl)-2-nitrobenzoic acid (NMSBA) product. Preferably, the silicate sorbent is contacted with the solution of 4-(methylsulfonyl)-2-nitrobenzoic acid (NMSBA) under conditions of neutral pH. The sorbent is effective in removing the impurities from the solution, to yield substantially pure 4-(methylsulfonyl)-2-nitrobenzoic acid (NMSBA).

However, it has been found that 4-(methylsulfonyl)-2-nitrobenzoic acid (NMSBA) prepared using methods (a) to (c) may be employed directly in the further processing steps with little or no intermediate treatment or purification being required, in particular, without the need to prepare an aqueous solution and contact with activated carbon and without any treatment with base to hydrolyze undesired impurities, as taught as being necessary in the prior art.

In one embodiment, the process scheme for the preparation of mesotrione of the present invention comprises one or more, preferably all of, the steps of:

(a) purifying 4-(methylsulfonyl)-2-nitrobenzoic acid (NMSBA) by recrystallization from solution in an organic solvent and/or by contact with a solid sorbent, preferably a magnesium silicate sorbent;

(b) preparing 4-(methanesulfonyl)-2-nitrobenzoyl chloride (NMSBC) by the reaction of 4-(methylsulfonyl)-2-nitrobenzoic acid (NMSBA) in dichloroethane by refluxing with N,N-dimethyl formamide (DMF) and thionyl chloride;

(c) preparing 3-oxocyclohex-1-enyl-4-(methylsulfonyl)-2-nitrobenzoate by the reaction of 4-(methanesulfonyl)-2-nitrobenzoyl chloride with cyclohexane-1,3-dione in dichloromethane, while adding trimethylamine; and (d) carrying out an enol ester rearrangement of 3-oxocyclohex-1-enyl-4-(methylsulfonyl)-2-nitrobenzoate in the presence of an organic solvent, moderate base, and a cyanide ion source to obtain mesotrione.

Mesotione prepared as described above may be recovered from the final reaction mixture, after the necessary treatments and purification steps, using any suitable technique known in the art.

A most suitable and preferred technique is crystallization. Suitable crystallization techniques include batch, semi-continuous and continuous. In one embodiment of the present invention, it is particularly preferred to use batch crystallization. Such a recrystallization process is easy to control using simple equipment, rather than the expensive and sophisticated apparatus required for semi-continuous or continuous recrystallization.

In particular, batch crystallization allows for a significantly better control of the impurities present in the mesotrione product, in turn reducing the requirement for recrystallization stages that must be employed when the final product does not meet the desired specification regarding the level of impurities. For example, batch crystallization allows the pH of the mesotrione solution to be monitored and controlled, ensuring the optimum production of mesotrione in high yield, without decomposing the mesotrione product.

In addition, batch to batch crystallization requires less analysis of the mesotrione product than the semi-continuous or continuous crystallization processes.

Still further, batch crystallization provides a repeatable product quality.

Finally, the mother liquor can be recycled from each batch with minimal treatment, for example distillation.

Accordingly, in a fourth aspect, the present invention provides a process for preparing mesotrione, the process comprising:

providing a solution of mesotrione in an organic solvent; and crystallizing mesotrione from the organic solvent batchwise.

Surprisingly, it has been found that it is not necessary to induce the crystallization of mesotrione by adding crystal seeds, as is considered necessary in the prior art, as long as the appropriate solvent is selected. In this case, an example of an appropriate solvent is toluene.

Preferably, the crystallization procedure is carried out by feeding a mesotrione solution at pH less than 7 into the batch crystallizer at a controlled rate, while maintaining the pH in the crystallizer between 2.5 and 4.0 by addition of an acid. The feed of the mesotrione solution is stopped when the level in the crystallizer reaches an upper limit, after which, the mesotrione slurry may be completely removed from the crystallizer until the volume in the crystallizer reaches a lower limit. Thereafter, the batch process may be restarted by recommencing the feed of mesotrione solution.

Mesotrione prepared using the process scheme of embodiments of the present invention is particularly suitable for use in formulating agrochemical compositions. Techniques for formulating the mesotrione composition are known in the art.

Embodiments of the present invention will now be described, for illustration purposes only, by way of the following Example.

In the following example, percentages are weight percent, unless otherwise indicated.

EXAMPLE

Example 1a

Preparation of 4-(Methanesulfonyl)-2-nitrobenzoyl chloride 4-(Methanesulfonyl)-2-nitrobenzoyl chloride (NMSBC) was prepared by the following general reaction scheme:

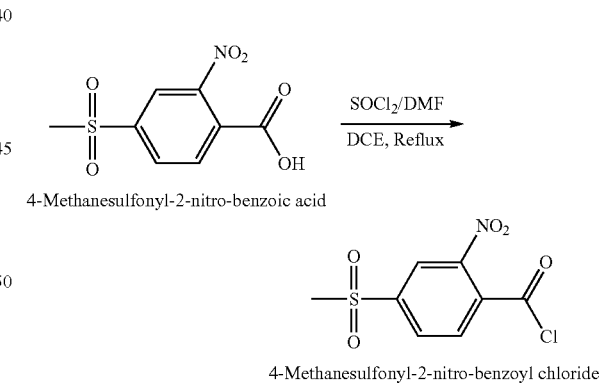

Dichloroethane (25 g) was charged into a clean glass flask predried using nitrogen gas, followed by 4-(methylsulfonyl)-2-nitrobenzoic acid (NMSBA) (10 g; 41 mmol). Thereafter, the mixture was stirred while adding in one lot a catalytic portion of N,N-dimethyl formamide (DMF) (0.1 g) and thionyl chloride (SOCl2) (9.7 g; 82 mmol) slowly over a period of 30 min. The reaction mixture was then slowly heated at such a rate that the temperature was raised to from 65 to 69° C. within 4 hours, until the reaction mixture refluxed. The gaseous by-products of sulphur dioxide and hydrogen chloride were removed by scrubbing with a caustic lye scrubber. The temperature of the mixture was maintained with stirring for another 2 hours, until the amount of unreacted 4-(methylsulfonyl)-2-nitrobenzoic acid (NMSBA) present was less than 0.1%, as determined by HPLC tracing analysis. After the reaction was completed, the solvent and unreacted thionyl chloride were removed under reduced pressure at a temperature below 60° C., until the amount of residual thionyl chloride was less than 0.1%.

The product 4-methanesulfonyl-2-nitro-benzoyl chloride (NMSBC) was obtained in an amount of 10.53 g (39.94 mmol). The yield was 98.2%.

Example 1b

Preparation of 3-Oxocyclohex-1-enyl-4-(methylsulfonyl)-2-nitrobenzoate

3-Oxocyclohex-1-enyl-4-(methylsulfonyl)-2-nitrobenzoate was prepared by the following general reaction scheme:

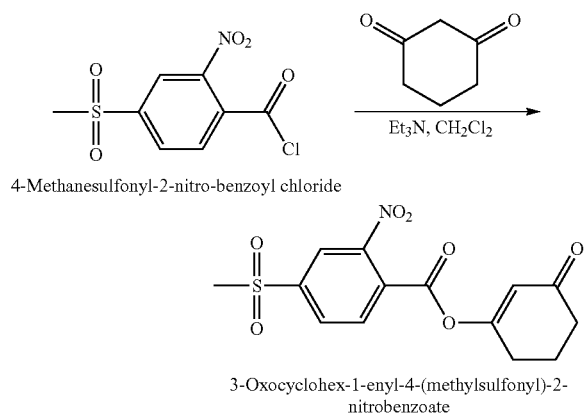

The 4-methanesulfonyl-2-nitro-benzoyl chloride (NMSBC) acquired from Example 1a (10.53 g, 39.94 mmol), cyclohexane-1,3-dione (4.5 g, 40.0 mmol) and dichloromethane (33.0 g) were charged into a 250 mL flask with stirring. When all solid raw materials were dissolved, triethyl amine (TEA) (5.22 g, 51.63 mmol) was added slowly through an addition funnel over a period of 4 to 5 hours. After the addition of triethyl amine (TEA) had been completed, the reaction was allowed to continue for another 3 hours with stirring at room temperature. The reaction mixture was washed with hydrochloric acid (2N, 8.2 mL), water (8.2 mL), aqueous potassium carbonate solution (5% $K_2CO_3$, 812 mL) and saturated sodium chloride solution (8.2 mL) in sequence. The organic phase was then percolated over anhydrous calcium chloride to remove free moisture. The solvent was then removed under reduced pressure to acquire the product.

3-Oxocyclohex-1-enyl-4-(methylsulfonyl)-2-nitrobenzoate was obtained in an amount of 13.22 g (39.01 mmol). The yield of this step was 97.5%.

Example 1c

Preparation of Mesotrione

The product acquired from Example 1b, 3-oxocyclohex-1-enyl-4-(methylsulfonyl)-2-nitrobenzoate, was then subjected to an enol ester rearrangement to form the product mesotrione, by the following general reaction scheme:

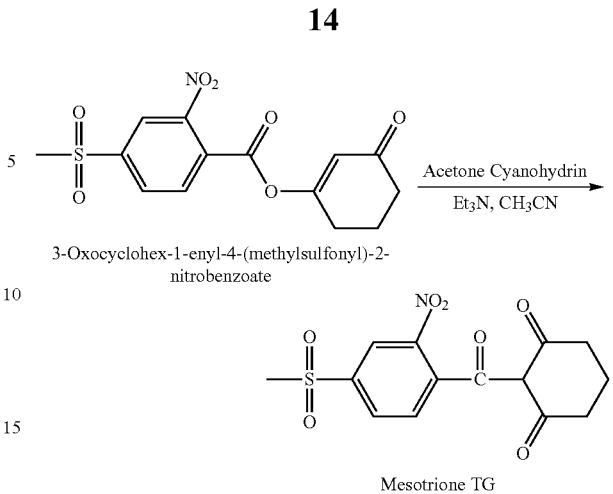

The product acquired from Example 1b, 3-Oxocyclohex-1-enyl-4-(methylsulfonyl)-2-nitrobenzoate) (13.22 g, 39.01 mmol) was dissolved with stirring in 25 g of acetonitrile, and was then charged to a glass flask predried under a nitrogen atmosphere. Triethyl amine (TEA) (3.92 g; 38.71 mmol) and acetone cyanohydrin (1.4 g; 16.3 mmol) were charged to the flask and the resulting mixture was stirred for 10 hours at room temperature until the rearrangement was complete. Thereafter, cyclohexane (25 g) was added to dilute the solution. The resulting solution was washed with hydrochloric acid (2N, 8.2 mL) and extracted with aqueous potassium carbonate solution (5% $K_2CO_3$, 16.4 mL) at a pH 6.8.

The aqueous phase was separated and acidified with hydrochloric acid (2N) to give a mesotrione product. The product was washed with toluene (2×20 mL) to remove impurities. Filtration of the resulting mixture, washing and drying under reduced pressure yielded the desired pure mesotrione product.

The mesotrione product was technical grade purity (TG) and was recovered in an amount of 7.34 g, 21.65 mmol. The yield of this step was 54%.

It will be noted that the entire process scheme to produce mesotrione was carried out in a series of simple steps, with minimal processing requirements under mild reactions conditions and using components that are readily available commercially and straightforward to handle.

Many modifications and variations of the present disclosure are possible in light of the above teachings and may be practiced otherwise than as specifically described while within the scope of the following claims.

The invention claimed is:

1. A process for the preparation of mesotrione enolate, the process comprising providing a solution of mesotrione in an organic solvent and contacting the solution with a moderate base in the presence of water at a pH of from 6 to 8, to form an aqueous mesotrione enolate solution, and wherein the mesotrione and the moderate base are present in a molar ratio of 1: equal to or less than 1.

2. The process according to claim 1, wherein the solvent is selected from an ether, a haloalkane, an alkane, a cycloalkane, or an organic nitrile.

3. The process according to claim 2, wherein the solvent comprises an ether selected from diethyl ethers, dimethyl ethers, dipropyl and diisopropyl ethers, butyl ethers, pentyl ethers, or petroleum ether.

4. The process according to claim 2, wherein the solvent comprises a haloalkane having from 1 to 8 carbon atoms.

5. The process according to claim 4, wherein the haloalkane comprises a chlorine substituent.

6. The process according to claim 4, wherein the haloalkane is selected from dichloromethane, dichloroethanes, dichloropropanes, dichlorobutanes, or dichloropentanes.

7. The process according to claim 2, wherein the solvent comprises an alkane and/or a cyclohexane.

8. The process according to claim 7, wherein the solvent comprises hexane, or cyclohexane.

9. The process according to claim 2, wherein the solvent comprises a nitrile having from 2 to 4 carbon atoms.

10. The process according to claim 9, wherein the solvent comprises acetonitrile.

11. The process according to claim 1, wherein the moderate base is selected from a trialkylamine, an alkali metal carbonate, an alkali metal phosphate, an alkaline earth metal carbonate, or an alkaline earth metal phosphate.

12. The process according to claim 11, wherein the moderate base comprises potassium carbonate.

13. The process according to claim 1, wherein the pH is in the range of from 6.2 to 7.6.

14. The process according to claim 1, wherein the mesotrione is prepared by an enol ester rearrangement of 3-oxocyclohex-1-enyl-4-(methylsulfonyl)-2-nitrobenzoate.

15. A process for preparing mesotrione comprising:
contacting the products of an enol ester rearrangement of 3-oxocyclohex-1-enyl-4-(methylsulfonyl)-2-nitrobenzoate with an organic solvent to dissolve mesotrione and form a resulting solution;
contacting the resulting solution from said contacting the products of an enol ester rearrangement step with an aqueous solution of an acid to form a washed mesotrione solution;
providing the washed mesotrione solution in an organic solvent to form a resulting solution; and
contacting the resulting solution from said providing the washed mesotrione solution step with a moderate base in the presence of water at a pH of from 6 to 8 to form an aqueous mesotrione enolate solution,
wherein the mesotrione and the moderate base are present in a molar ratio of 1: equal to or less than 1.

16. The process according to claim 15, wherein the organic solvent in said contacting the products of an enol ester rearrangement step is selected from an ether, a haloalkane, an alkane, a cycloalkane, an organic nitrile, an organic amide, or an alkyl or di-alkyl sulphonamide.

17. The process according to claim 15, wherein the acid is a mineral acid.

18. The process according to claim 15, further comprising carrying out an enol ester rearrangement of 3-oxocyclohex-1-enyl-4-(methylsulfonyl)-2-nitrobenzoate in the absence of a phase transfer catalyst, a transition metal salt and an azole.

19. The process according to claim 15, wherein the moderate base is selected from an alkylamine, an alkali metal carbonate, or an alkali metal phosphate.

20. The process according to claim 19, wherein the moderate base comprises potassium carbonate.

21. The process according to claim 1, wherein the molar ratio of mesotrione to moderate base is 1: 0.75 to 0.95.

22. The process according to claim 21, wherein the molar ratio of mesotrione to moderate base is 1:0.8.

23. The process according to claim 15, wherein the organic solvent in said providing the washed mesotrione solution step is selected from an ether, a haloalkane, an alkane, a cycloalkane, or an organic nitrile.

24. The process according to claim 23, wherein the organic solvent in said providing the washed mesotrione solution step comprises an ether selected from diethyl ethers, dimethyl ethers, dipropyl and diisopropyl ethers, butyl ethers, pentyl ethers, or petroleum ether.

25. The process according to claim 23, wherein the organic solvent in said providing the washed mesotrione step comprises a haloalkane having from 1 to 8 carbon atoms.

26. The process according to claim 23, wherein the organic solvent in said providing the washed mesotrione step comprises an alkane and/or a cycloalkane having from 4 to 8 carbon atoms.

27. The process according to claim 23, wherein the organic solvent in said providing the washed mesotrione step comprises a nitrile having from 2 to 4 carbon atoms.

* * * * *